(12) United States Patent
Bammerlin et al.

(10) Patent No.: US 7,694,812 B2
(45) Date of Patent: Apr. 13, 2010

(54) EXTERNAL CONTAINER FOR AN IMPLANT CARRIER

(75) Inventors: Rainer Bammerlin, Kandern (DE); Daniel Gunter, Waldenburg (CH)

(73) Assignee: Straumann Holding AG Peter, Basel (CH)

( * ) Notice: Subject to any disclaimer, the term of this patent is extended or adjusted under 35 U.S.C. 154(b) by 0 days.

(21) Appl. No.: 12/195,592

(22) Filed: Aug. 21, 2008

(65) Prior Publication Data

US 2009/0065387 A1 Mar. 12, 2009

(51) Int. Cl.
*A61C 19/02* (2006.01)
(52) U.S. Cl. .................. 206/368; 206/63.5; 206/493
(58) Field of Classification Search ............ 206/368, 206/369, 63.5, 493, 806, 438, 363
See application file for complete search history.

(56) References Cited

U.S. PATENT DOCUMENTS 6,428,318 B2 * 8/2002 Artal ..................... 433/173

6,955,258 B2 * 10/2005 Howlett et al. ............. 206/63.5
2002/0025505 A1 * 2/2002 Beaty et al. ................. 433/173

FOREIGN PATENT DOCUMENTS

| DE | 102007037593.1-43 | 8/2007 |
| EP | 1145692 A2 | 10/2001 |
| EP | 1252866 A1 | 10/2002 |
| EP | 0986341 B1 | 11/2004 |
| EP | 1523955 A1 | 4/2005 |
| EP | 08162751.5 | 2/2009 |
| WO | WO 00/02496 | 1/2000 |
| WO | WO 2006/052478 A1 | 5/2006 |

* cited by examiner

*Primary Examiner*—Jacob K Ackun, Jr.
(74) *Attorney, Agent, or Firm*—Lisa V. Mueller; Polsinelli Shughart (57) ABSTRACT

The present invention refers to an external container (1) for an implant carrier (20), comprising a cylindrical body portion (10) and a lid (50) closing the cylindrical body portion (10), the lid (50) being provided with a truncated cone-like element (74) which protrudes into the cylindrical body portion (10) and has on its surface at least one annular means (73) for fixing an implant carrier (20) into place which is adapted such as to fix the implant carrier (20) releasably into place in a stable position in the center of the interior of the cylindrical body portion (10).

13 Claims, 7 Drawing Sheets

EXTERNAL CONTAINER FOR AN IMPLANT CARRIER

FIELD OF USE OF THE INVENTION

The present invention refers to an external container for receiving an implant carrier, in particular implant carriers for dental technology or dental implant carriers which receive a screw-shaped or cylindrical implant. This external container is used to protect the implant carrier with the implant attached to it from outer influences, such as damaging and/or contamination.

The function of such external containers is to safely carry the implant assembly, comprising the dental implant, the implant carrier and a holding element, and to provide a sterile environment for storage. To remove the implant carrier during surgery, the implant carrier is taken from the external container, then the dental implant is taken from the implant carrier and positioned in the implantation site in the patient; finally, the holding element is removed.

STATE OF THE ART

From EP 1 523 955, an external container for an implant carrier is known where an outer capsule is threadedly closed with a lid. For secure closure, the lid is screwed and, if necessary, glued to the cylindrical body portion. In addition, the external container has a button for releasing the implant carrier. The lid is formed in two parts, where a first part forms the lid for threading to the cylindrical body portion and a second part adapted as a button can release the implant carrier located within the external container. A ring-shaped element located on a tongue of the lid engages in a corresponding recess on the implant carrier when the lid is screwed on, thus fixing the implant carrier into place in the external container and holding it when the implant carrier is removed. A consequence of the threaded connection, however, is that the ring-shaped element is moved from a relaxed storage state by firm screwing of the lid. Due to the force acting continuously during screwing, the spring is worn out, losing its elasticity since it constantly remains in a tensioned state. Therefore, the implant carrier can fall down from the lid when it is taken out or the lid is screwed off, since the retaining force would not be sufficient anymore. In addition, such implants must be maintained sterile until implantation and have, among others, very delicate structures, and consequently, an external container must provide both an aseptic environment and shock resistance in order to prevent damaging of the implant.

SUMMARY OF THE INVENTION

The object of the present invention is to overcome the above-mentioned disadvantages of known external containers for implant carriers and to provide an external container which prevents a falling out from the implant carrier, enables prolonged storage and avoids material fatigue.

Within the framework of this object, another object of the present invention is to provide an external container for an implant carrier having an improved connection technique between the external container and the implant carrier.

Within the framework of this object, an additional object of the present invention is to implement a hermetic external container for an implant carrier, to be filled with a protective fluid.

Another object of the present invention is that the external container for an implant carrier can be produced easily and inexpensively with conventional processes and materials.

The objects mentioned above as well as other objects to be found in the following description are fulfilled by an external container for an implant carrier according to claim 1. Other advantageous embodiments of the present invention are set out in the dependent claims.

SHORT DESCRIPTION OF THE FIGURES

Other features and advantages of the present invention as well as the mode of operation of the exemplary embodiments of the present invention are described below with reference to the accompanying drawings.

The accompanying drawings exemplify the present invention and are used, together with the description, to explain the basic principles of the invention and enable a person skilled in the relevant art to manufacture and use the invention. For the sake of simplicity, identical elements in successive figures are normally not designated as such, as long as they can be clearly identified as "repetitive elements".

In these figures.

DESCRIPTION OF PREFERRED EMBODIMENTS OF THE INVENTION

Based on the following FIGS. 1 through 3D, a currently preferred embodiment of the present invention of an external container 1 for an implant carrier 20 is described, consisting of a substantially cylindrical body portion 10 and a lid 50 which is screwed onto the cylindrical body portion 10.

Figure 1:
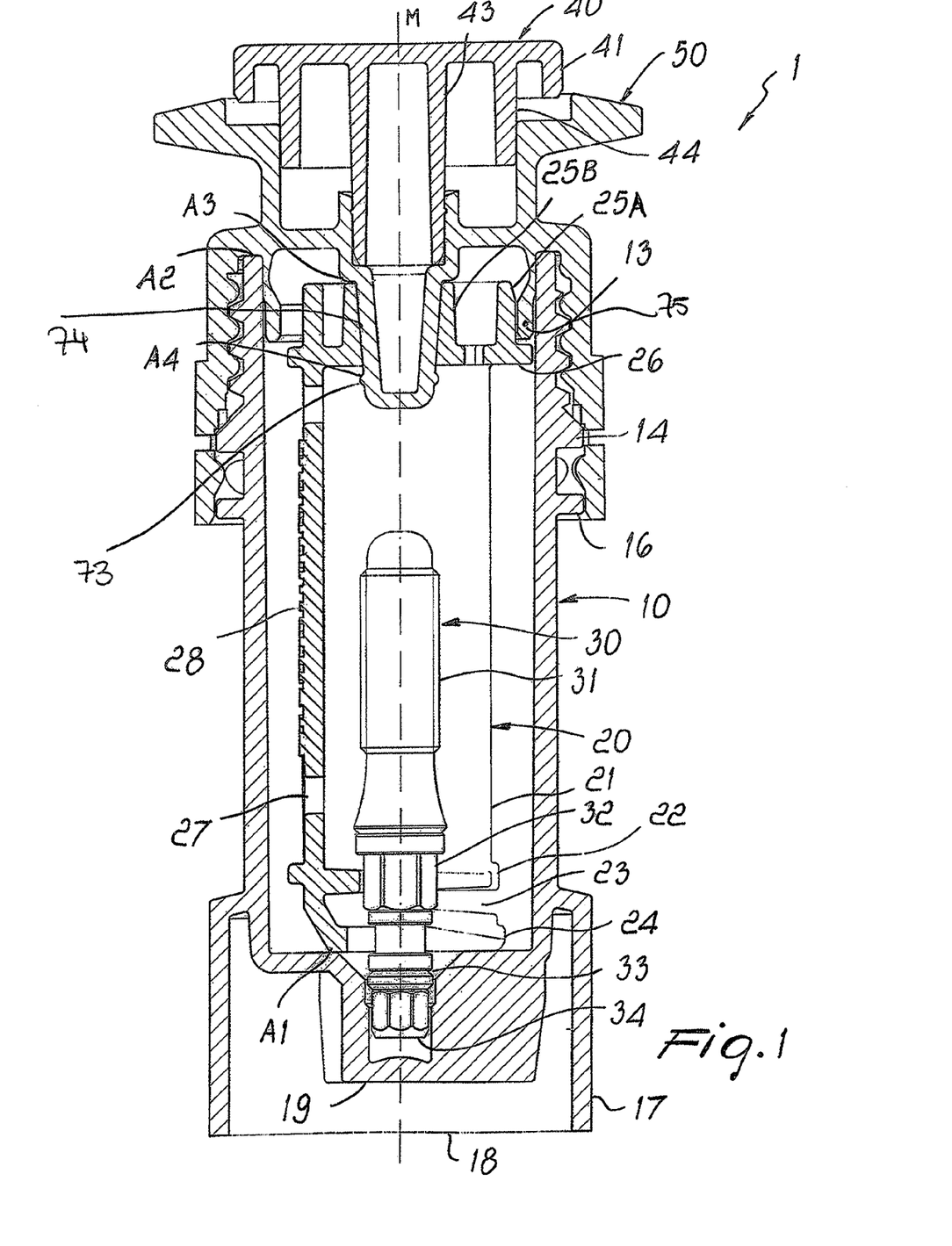
FIG. 1 shows a longitudinal section of an external container for an implant carrier according to an embodiment of the invention.
Figure 1A:
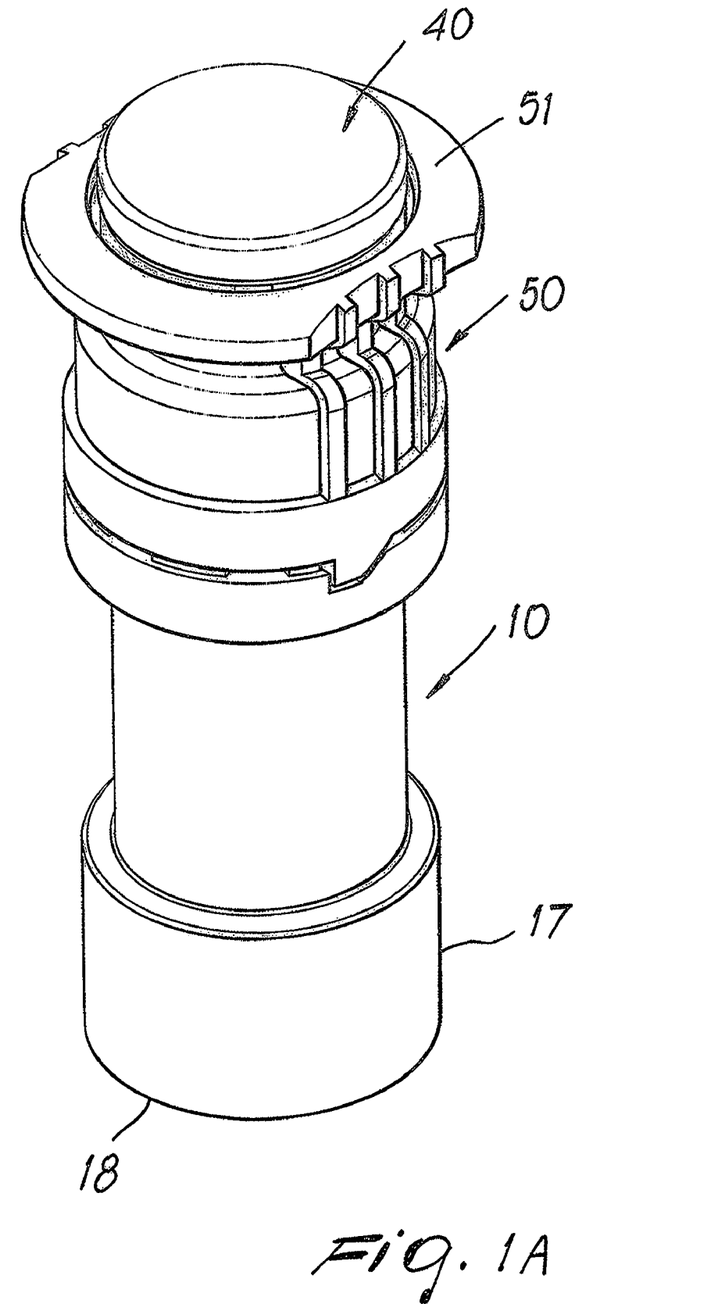
FIG. 1A shows a perspective view of an external container for an implant carrier according to FIG. 1.

FIG. 1 shows a longitudinal section of an external container 1 for an implant carrier 20 with a dental implant 30 fixed into place therein. The dental implant 30 is provided with a thread 31 (in the following second thread) to be screwed into the jaw of a patient, the dental implant 30 being screwed onto a holding element 32 and the part of the dental implant 30 which is to be implanted being enclosed within the implant carrier 20. The implant carrier 20 has a carrier shaft 21 in which the dental implant 30 is positioned. On one side, the carrier shaft 21 borders on a jaw-like portion 23 which is formed between a first plate 22 and a second plate 24 and is used to slide in the dental implant 30. On the side, where the reinforcing ribs 28 are arranged, an opening 27 is also arranged. To fix the holding element 32 into place, an implant holder 19 is provided within a cylindrical foot 17, in which implant holder a polygonal area 34 of the holding element 32 is inserted, where for additional stabilization of the holding element 32, a support ring 33 is inserted on the insertion opening of the implant holder 19. The implant carrier 20 inserted in the external container 1 is supported by the surface of the implant holder 19 facing the interior of the external container 1, thus forming a first stop A1 which is suitable for bonding. A second stop A2 is formed on the enclosing wall edge 12 (FIG. 2) which, when the lid 50 is screwed on, can also advantageously be bonded with a section of the lid 50 located between a tongue-like element 75 and a thread 65 (in the following called third thread). A first rotationally symmetrical area 25A and a second rotationally symmetrical area 25B are arranged together on a reinforcing plate 26 of the implant carrier 20. For further fixing into place, a third stop A3, located on the interface between the second rotationally symmetrical area 25B and the edge which is formed between an element 74 of the lid 50, which is truncated cone-like and described in the following, and a first cavity 76 of the lid 50, also described in the following, can also be bonded. The area of an annular sleeve 73 of the lid 50, described in the following, forms a fourth stop A4 with the implant carrier 20 placed on the implant, which stop can also be advantageously bonded. For filling the cylindrical body portion 10 with a protective fluid, at least the first stop A1 should be bonded in order to produce a hermetic area within the cavity of the cylindrical body portion 10 so that no fluid can escape from the external container 1. The cylindrical body portion 10 is provided, on the side facing the lid 50, with a thread 13 (in the following called first thread) for threadingly fixing the lid 50 into place on the cylindrical shaft 10, the lid 50 in the screwed-on state being in contact with a first bead 14 and a second bead 16. A button 40, having a button side wall 41 and a stabilizing sleeve 43 and an intermediate sleeve 44, can be plugged onto the lid 50 as described below in connection with FIG. 3A. It can advantageously be provided with color-coding for identifying various dental implants 30 located in the external container 1, which is achieved e.g. by the use of color-codings and/or designations for identifying a dental implant (not shown). FIG. 1A shows for illustration purposes the elements already described from FIG. 1 in a perspective view. The lid 50 can also be bonded to the button 40 or formed as one piece.

Figures 2, 2A:
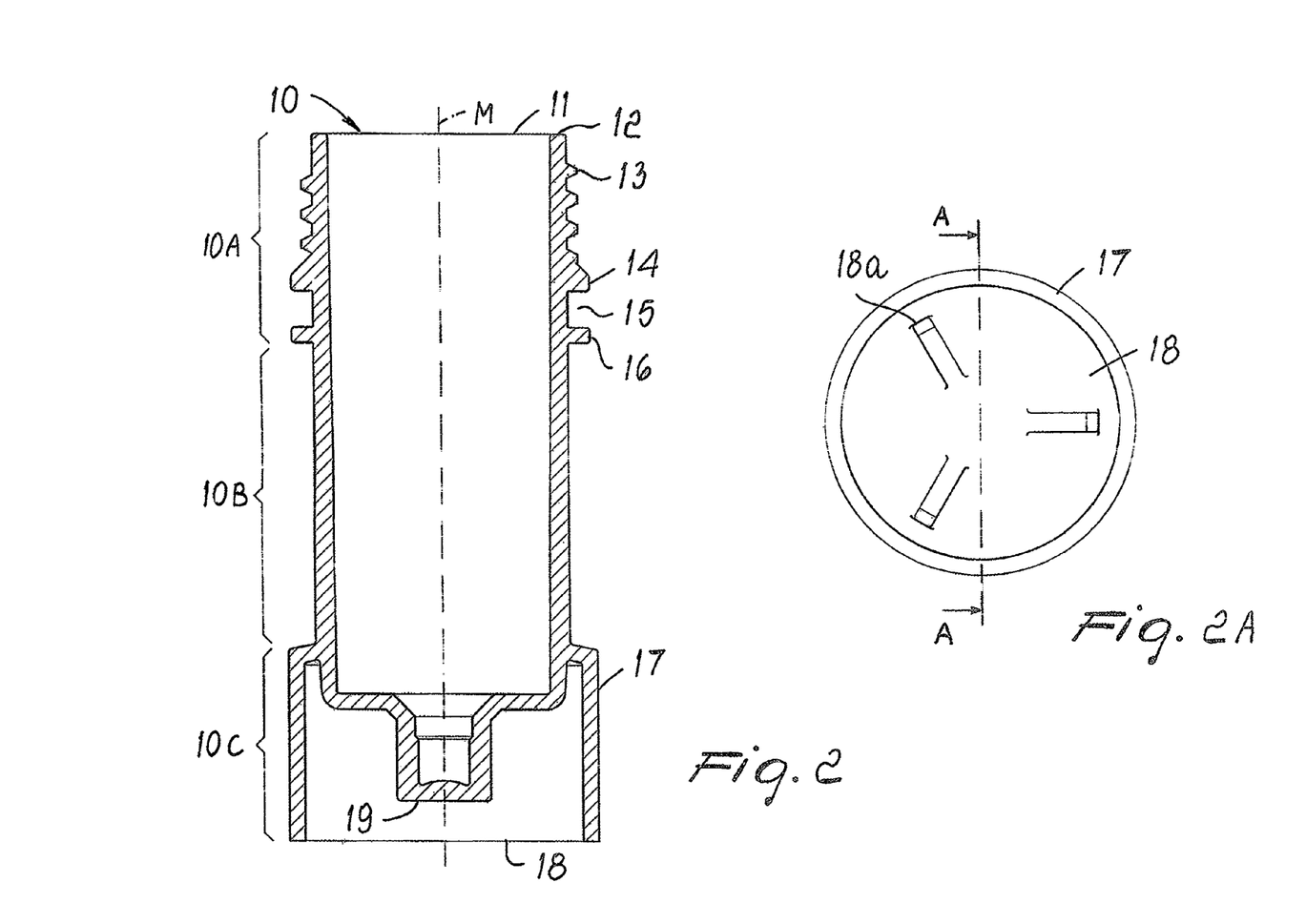
FIG. 2 shows a longitudinal section of a cylindrical body portion of an external container, taken along line A-A according to FIG. 2A.
FIG. 2A shows a bottom view of a cylindrical body portion of an external container according to FIG. 2.
Figure 2B:
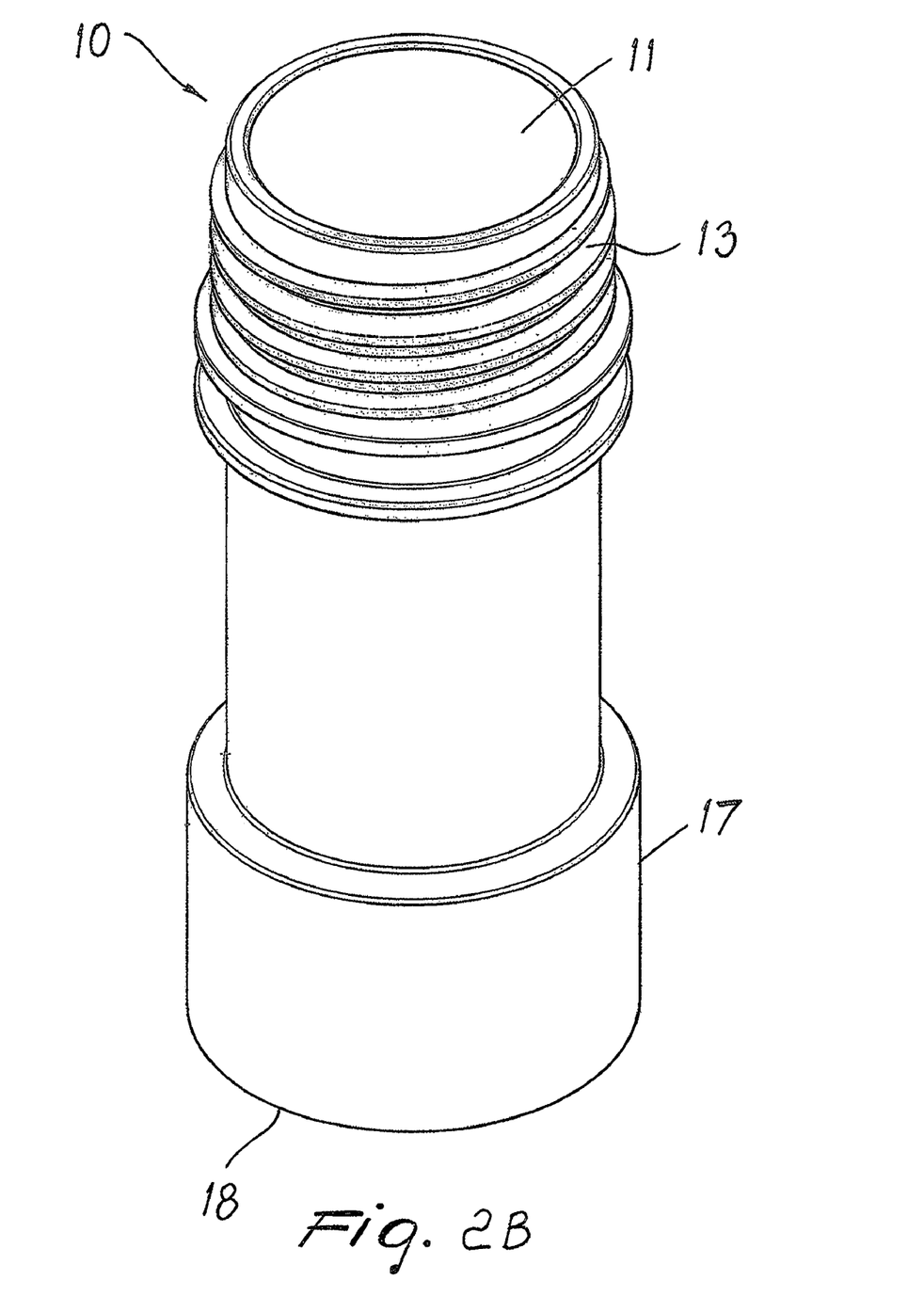
FIG. 2B shows a perspective view of a cylindrical body portion of an external container according to FIG. 2.

FIG. 2 shows the cylindrical body portion 10 in longitudinal section, taken along line A-A of FIG. 2A, which is divided in three portions, namely:

a fixing portion 10A comprising the first thread 13 for screwing on the lid 50 and the first bead 14 forming the end of the first thread 13. Between the second bead 16, a recess 15 is located in which drop-shaped convexities 70/70A (FIG. 3B) of a securing ring 56 of the lid 50 are locked into place and supported on the second bead 16.

a shaft portion 10B formed substantially by a cylindrical hollow body, a bottom portion 10C bordering on the shaft portion 10B and comprising a cylindrical foot 17 with an implant holder 19 enclosed therein and the bottom plate 18, wherein, as shown in FIG. 2A, at least 3 impressions 18A are formed in the bottom plate 18, which impressions are arranged radially at an angle of 120 degrees and used for insertion in a transport holder (not shown). FIG. 2B shows the cylindrical body portion 10 in a perspective view, the opening 11 being used for insertion of the implant carrier 20 or for filling in a protective fluid, respectively.

Figure 3:
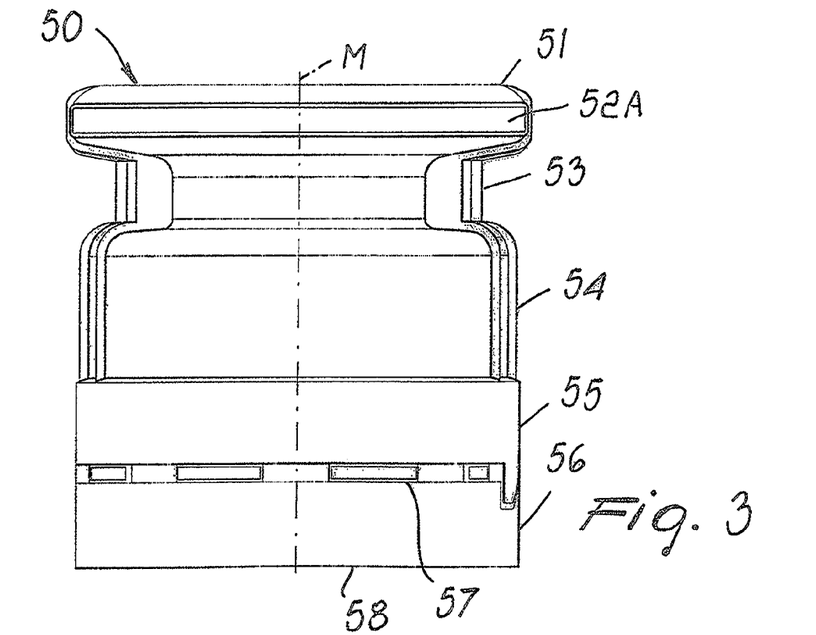
FIG. 3 shows a side view of a lid of an external container according to an embodiment of the invention.
Figure 3A:
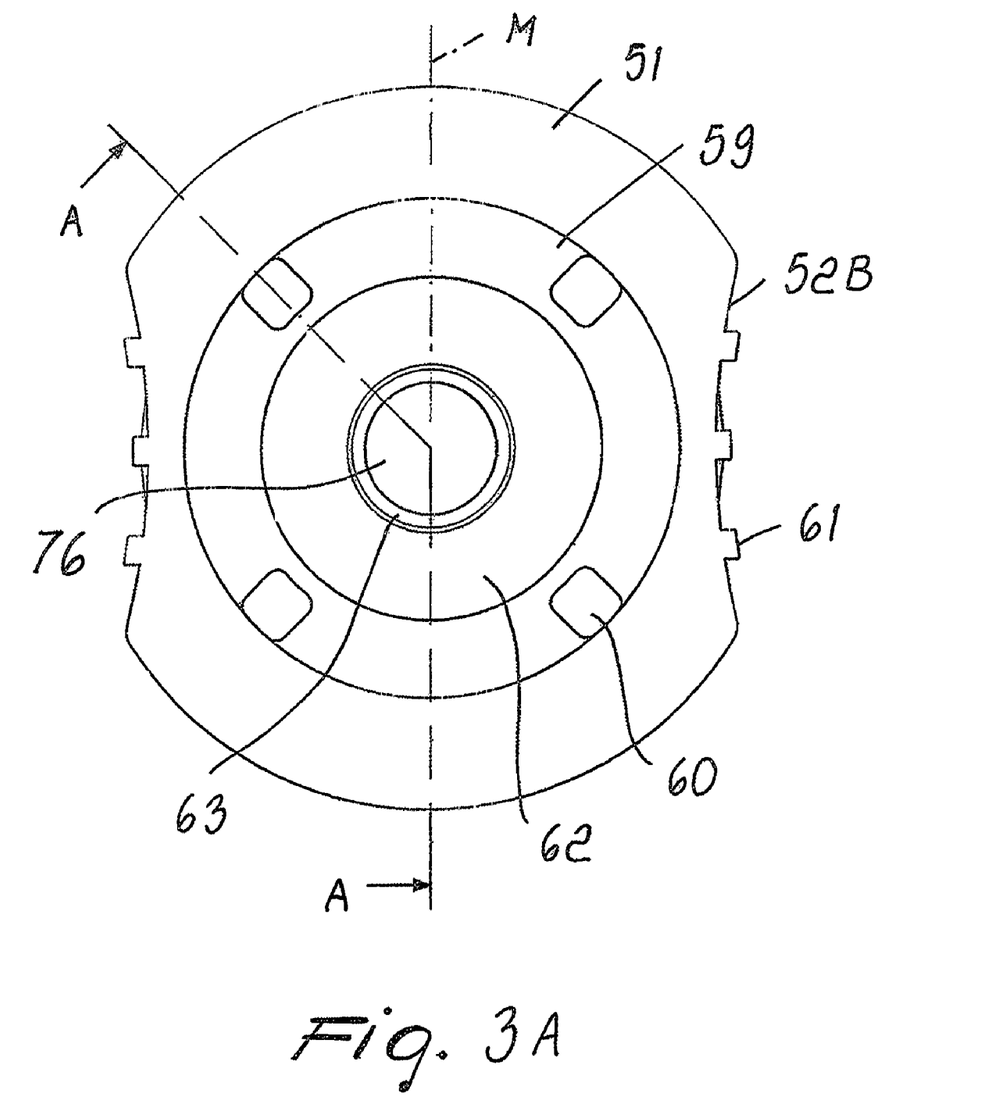
FIG. 3A shows a top view of a lid of an external container according to FIG. 3.
Figure 3B:
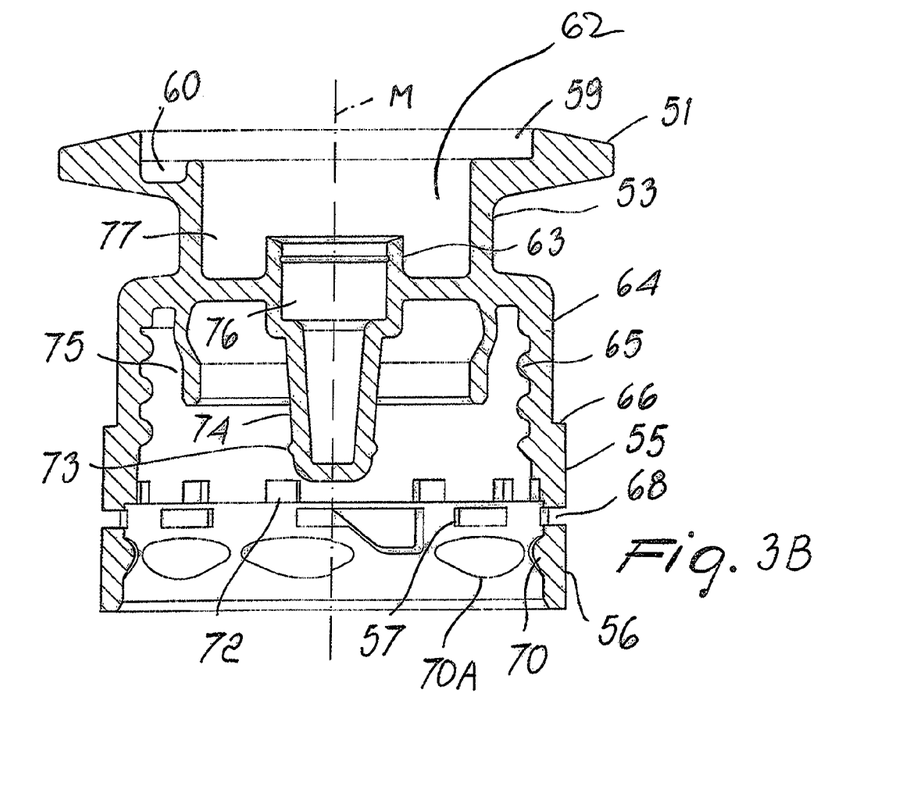
FIG. 3B shows a sectional view of a lid of an external container, taken along line A-A according to FIG. 3A.

FIG. 3 shows a lateral view of a lid 50 of an external container 1 having a chamfered end face 51 bordering on an end face edge 52A, a neck 53 being formed between the end face 51 and the cap-shaped portion 64 of FIG. 3B. The cap-shaped portion 64 has, on its outer surface, stripe-shaped gripping means 54 providing a good grip both when the lid 50 is screwed on and off. The cap-shaped portion 64 borders on a lid removal portion 55 with connected securing ring 56. In the area between lid removal portion 55 and securing ring 56, there is a breaking point 57 in the form of rectangular cutouts which are arranged in a perimetrically circumferential recess 68 and which are suitable for releasing the lid 50. The securing ring 56 has a lower edge 58 on its bottom end.

FIG. 3A shows further features of the lid 50 in a top view, where the substantially chamfered end face 51 is interrupted by two end face edge recesses 52B (see FIG. 3B), arranged symmetrically to the central axis M and provided on their surfaces with at least one spigot 61 (see FIG. 3B). Connected to the end face 51 in center direction there is a first trough 59 which transitions to a second trough 62. A rotationally symmetrical spigot 63 protrudes from the center of the second trough 62. The rotationally symmetrical spigot 63 has in its interior a first cavity 76 which is suited for positive engagement of the stabilizing sleeve 43 in FIG. 1. The rotationally symmetrical spigot 63, together with the first 59 and the second 62 trough, form a container for the detachable button 40 which, by means of an attached coding, e.g. color-coding, identifies various dental implants located in the external container 1 and unambiguously marks the different kinds of dental implants 30.

FIG. 3B shows a sectional view of the lid 50 of an external container 1, taken along line A-A in FIG. 3A, the lid 50 being provided in its center with a truncated cone-like element 74 on which the implant carrier 20 can be placed, as shown in FIG. 1. On one end facing the cylindrical body portion 10, there is at least one annular sleeve 73 which protrudes from the surface. In a preferred embodiment, the annular sleeve 73 is formed as a continuous perimetrical contour edge. Alternatively, the annular sleeve 73 can also be formed by a plurality of perimetrical convexities.

Between the truncated cone-like element 74 and the portion of the lid with the first thread 13, a tongue-like element 75 is arranged which, in the assembled state, is in contact with a first substantially rotationally symmetrical area 25A (FIG. 1) of the implant carrier 20 with a certain clearance and is used to guide the implant carrier 20 during insertion. In addition, there is a space between the reinforcing plate 26 and the lower area of the tongue-like element 75 in the assembled state.

In this way, when the lid 50 is screwed on, the entire screwing force is absorbed by the first thread 13 of the implant carrier 20 and the third thread 65 of the lid 50, so that no additional force is exerted on the tongue-like element 75. A second cavity 77 of the lid 50 is used to receive the intermediate sleeve 44 of the button 40, shown in FIG. 1. The cap-shaped area 64 is connected to the neck 53 and followed by a step 66 bordering on the lid removal portion 55.

Figure 3C:
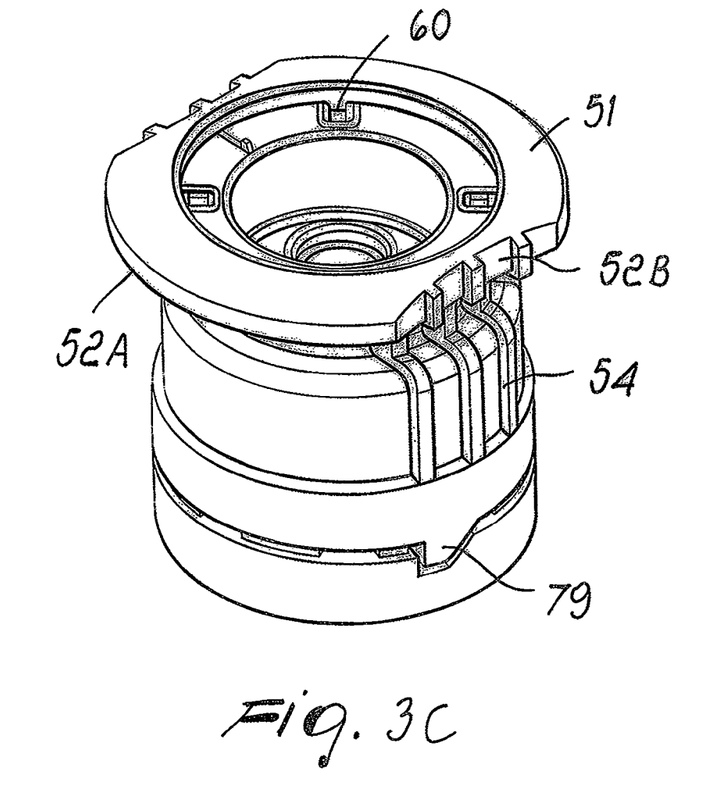
FIG. 3C shows a perspective top view of a lid of an external container according to FIG. 3.

FIG. 3C shows a perspective top view of the lid 50, a plurality of recesses 60 being arranged symmetrically in the surface of the first trough 59 which are suitable to fix the lid 50 into place. On the lid removal portion 55, a snap-in pin 79 bordering on the perimetrically circumferential recess 68 (FIG. 3D) is arranged which engages a recess in the securing ring 56. The purpose of the snap-in pin 79 is to definitely determine the direction of rotation of the lid 50 with reference to the securing ring 56.

Figure 3D:
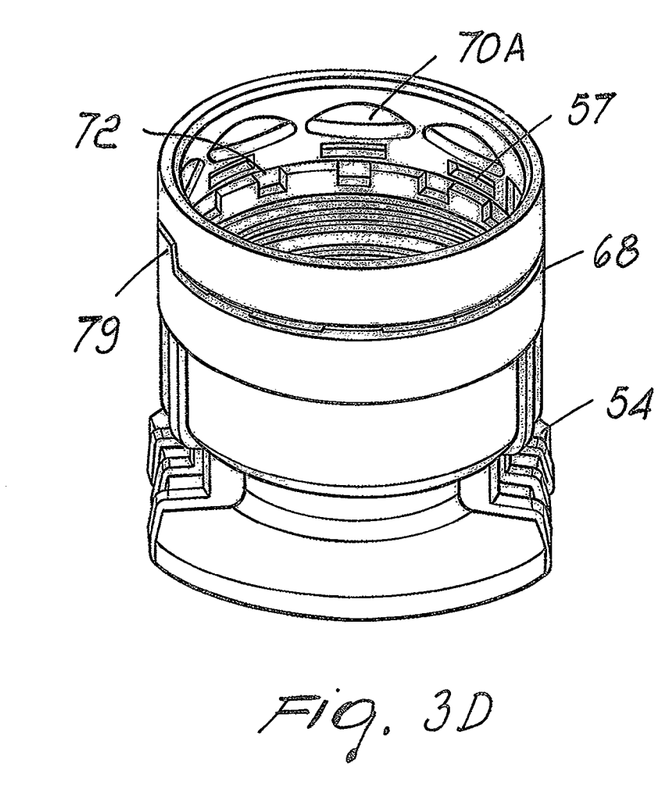
FIG. 3D shows a perspective bottom view of a lid of an external container according to FIG. 3.

FIG. 3D shows a perspective bottom view of a lid 50 of the external container 1, the securing ring 56 represented in FIG. 3 presenting, on its inner surface, on the circumferential area facing the cylindrical body portion 10, drop-shaped convexities 70 and 70A which are suitable to be locked into place in the recess 15 represented in FIG. 2. The purpose of reference number 70 is to illustrate the drop-shaped convexities in the sectional representation. Adjacent to the drop-shaped convexities 70A, the breaking point 57 is located in the direction of the body interior of the lid 50, and between the drop-shaped convexities 70A and the third thread 65, a merlon-shaped portion 72 is formed which, in the screwed state of lid 50 and cylindrical body portion 10, engages the first bead 14.

The components of the external container 1, consisting of cylindrical body portion 10, lid 50 and button 40, can advantageously be manufactured with conventional methods, e.g. casting, and are preferably made of plastic. A possible plastic material for the external housing is cyclo-olefin copolymer (COC), which is FDA- and CE-certified; as medically usable materials and for the cap, high-density polyethylene (HDPE) or low-density polyethylene (LDPE) can be employed, but also other materials having the same or similar properties.

According to a presently preferred embodiment of the invention, an external container 1 for an implant carrier 20 is provided comprising: a cylindrical body portion 10 and a lid 50 closing the cylindrical body portion 10, the lid 50 being provided with a truncated cone-like element 74 which protrudes into the cylindrical body portion 10, the implant carrier 20 presenting a hole 25B formed complementary to the truncated cone-like element 74, which hole surrounds the truncated cone-like element 74 with a close fit when the implant carrier 20 is attached to the lid 50, and wherein the truncated cone-like element 74 presents an annular sleeve 73 which engages behind the hole 25B with a space when the implant carrier 20 is attached to the lid 50.

If technical features mentioned in any of the claims are provided with a reference number, these reference numbers have been merely included to increase comprehensibility of the claims. Accordingly, these reference numbers have no limiting effect on the scope of each element which, by way of example, is identified by such reference numbers.

The invention claimed is:

1. External container for an implant carrier, comprising a cylindrical body portion and a lid closing the cylindrical body portion, the lid being provided with a truncated cone-like element which protrudes into the cylindrical body portion and which has, on its surface, at least one annular means for fixing an implant carrier into place which is adapted such as to fix the implant carrier into place releasably in a stable position in the center of the interior of the cylindrical body portion.

2. External container for an implant carrier according to claim 1, wherein a second, inwardly facing rotationally symmetrical portion of the implant carrier is held axially between a stop A3 on the base of the truncated cone-like element and the annular sleeve.

3. External container for an implant carrier according to claim 1, wherein the annular means is formed as a continuous perimetrical contour edge.

4. External container for an implant carrier according to claim 2, wherein the annular means is formed as a continuous perimetrical contour edge.

5. External container for an implant carrier according to claim 1, wherein the annular means is formed by a plurality of perimetrical convexities.

6. External container for an implant carrier according to claim 2, wherein the annular means is formed by a plurality of perimetrical convexities.

7. External container for an implant carrier according to claim 1, wherein the lid has a tongue-like element in contact with a first, outwardly facing, substantially rotationally symmetrical portion of the implant carrier.

8. External container for an implant carrier according to claim 7, wherein the tongue-like element for guiding the implant carrier is elastically deformable in the direction opposite to the central axis M of the external container.

9. External container for an implant carrier according to claim 1, wherein at least one first stop A1 on the external container and one second stop A2 on the lid fix the implant carrier into place in a stable position.

10. External container for an implant carrier according to claim 9, wherein the cylindrical body portion is filled with a fluid for storage.

11. External container for an implant carrier according to claim 9, wherein the fluid for storage is an electrolyte.

12. External container for an implant carrier according to claim 1, wherein the production material is a high-density poly-ethylene (HDPE) or a low-density polyethylene (LDPE) plastic.

13. External container for an implant carrier according to claim 1, wherein the lid is provided with a truncated cone-like element which protrudes into the cylindrical body portion, the implant carrier having a hole formed complementary to the truncated cone-like element which surrounds the truncated cone-like element in a close fit when the implant carrier is attached to the lid, and wherein the truncated cone-like element has an annular means which engages behind the hole with a space when the implant carrier is attached to the lid.

* * * * *